US012797498B2

(12) United States Patent
Lee et al.

(10) Patent No.: US 12,797,498 B2
(45) Date of Patent: Nov. 17, 2026

(54) MOBILE BIDIRECTIONAL STERILIZATION DEVICE AND VEHICLE EQUIPPED WITH SAME

(71) Applicants: HYUNDAI MOTOR COMPANY, Seoul (KR); KIA CORPORATION, Seoul (KR); KOLON INDUSTRIES, INC., Seoul (KR); DUCK YANG INDUSTRY CO., LTD., Ulsan (KR)

(72) Inventors: Jae-Seung Lee, Hwaseong-si (KR); Byoung-Chul Park, Seosan-si (KR); Jae-Yong Lee, Suwon-si (KR)

(73) Assignees: Hyundai Motor Company, and, Seoul (KR); Kia Corporation, and, Seoul (KR); Kolon Industries, Inc., and, Seoul (KR); Duck Yang Industry Co., Ltd., Ulsan (KR)

( * ) Notice: Subject to any disclaimer, the term of this patent is extended or adjusted under 35 U.S.C. 154(b) by 240 days.

(21) Appl. No.: 18/514,864

(22) Filed: Nov. 20, 2023

(65) Prior Publication Data

US 2025/0018071 A1 Jan. 16, 2025

(30) Foreign Application Priority Data

Jul. 11, 2023 (KR) ........................ 10-2023-0089767

(51) Int. Cl.

| | |
|---|---|
| ***A61L 2/10*** | (2026.01) |
| ***B60Q 3/68*** | (2017.01) |
| ***B60S 3/00*** | (2006.01) |

(52) U.S. Cl.
CPC .................. *A61L 2/10* (2013.01); *B60Q 3/68* (2017.02); *B60S 3/008* (2013.01)

(58) Field of Classification Search
CPC ... A61L 2/08; A61L 2/084; A61L 2/10; A61L 2/26; A61L 2202/11; A61L 2202/15; A61L 2202/16; B06Q 3/68; B60R 11/0241; B60R 16/03; B60R 2011/0005; B60R 2011/0094; B60S 3/008; B60Y 2306/05
(Continued)

(56) References Cited

U.S. PATENT DOCUMENTS

| | | | | |
|---|---|---|---|---|
| 2014/0264075 A1* | 9/2014 | LaPorte | .................... | A61L 2/00 250/455.11 |
| 2020/0087031 A1* | 3/2020 | Yoo | ........................ | A45D 44/00 |

(Continued)

FOREIGN PATENT DOCUMENTS

| | | |
|---|---|---|
| KR | 10-1517694 | 5/2015 |

*Primary Examiner* — Jason L McCormack
(74) *Attorney, Agent, or Firm* — Fish & Richardson P.C.

(57) ABSTRACT

A mobile bidirectional sterilization device includes a removable mobile bidirectional sterilization device in which a light guiding plate made of a light guiding film is connected from a power charger to a hinged cover through a curved connection section to emit visible light of a light-emitting diode (LED) to front, rear, and lateral surfaces of a mobile device or a fixed mobile bidirectional sterilization device in which the light guiding plate made of the light guiding film emits the visible light of the LED to the rear and front surfaces of the mobile device at a console bracket and a center fascia charger, solves a problem of harmfulness to the human body and a problem of directivity and transmittance due to an omnidirectional sterilization effect of the mobile device by the visible light with a 405 nm wavelength.

7 Claims, 5 Drawing Sheets

(58) Field of Classification Search
USPC .......................................... 250/455.11, 453.11
See application file for complete search history.

(56) References Cited

U.S. PATENT DOCUMENTS

| | | | | |
|---|---|---|---|---|
| 2021/0387507 | A1* | 12/2021 | Schleicher | H04B 1/036 |
| 2022/0072184 | A1* | 3/2022 | Groves | A61L 2/08 |
| 2022/0096693 | A1* | 3/2022 | Parker | A61L 2/10 |

* cited by examiner

<PROCESS: VEHICLE SEPARATED TYPE>

<PROCESS: VEHICLE INTEGRATED TYPE>

MOBILE BIDIRECTIONAL STERILIZATION DEVICE AND VEHICLE EQUIPPED WITH SAME

CROSS-REFERENCE(S) TO RELATED APPLICATIONS

This application claims priority to Korean Patent Application No. 10-2023-0089767, filed on Jul. 11, 2023, which is incorporated herein by reference in its entirety.

TECHNICAL FIELD

The present disclosure relates to a mobile sterilization device, and more particularly, to a vehicle equipped with a mobile bidirectional sterilization device for simultaneously emitting visible light with a 405 nm wavelength in upward and downward directions of a mobile device.

BACKGROUND

Recently, there has been a growing trend in integrating a mobile sterilization device with both a charging function and a sterilization function into vehicles.

This development arises from increasing concerns about hygiene issues related to various germs, including colon *Bacillus, Bacillus pyocyaneus*, and *Staphylococcus aureus*, due to the frequent handling of mobile devices, such as smart phones and mobile phones, by hands.

The mobile sterilization device, designed to address hygiene concerns, is strategically positioned within the vehicle's center fascia, specifically in front of the console armrest. This device includes an ultraviolet C (UVC) light-emitting diode (LED) unit equipped for sterilization, a mobile pedestal intended for mobile devices such as smart phones and mobile phones, and a reflector made of an aluminum material.

The UVC LED unit emits UVC light onto the mobile devices (e.g., smart phones and mobile phones) placed on the mobile pedestal, while the reflector enhances sterilization efficiency by concentrating and reflecting the emitted UVC light.

However, it is important to note that the UVC light, with a wavelength ranging from 100 nm to 280 nm for sterilization, poses potential health hazards and exhibits directional limitations depending on an LED mounting position. It also struggles with light transmission and diffusion.

Furthermore, since the UVC LED unit emits the UVC light from top to bottom, the mobile sterilization device faces a challenge in simultaneously sterilizing both the front and rear surfaces of mobile devices (e.g., smart phones and mobile phones).

SUMMARY

The present disclosure is directed to a mobile bidirectional sterilization device can include a power charger configured to charge a mobile device by connecting vehicle power, a cover configured to open the power charger, a first sterilization light generator provided at the cover and configured to generate visible light emitted downward toward a front surface of the mobile device, a second sterilization light generator provided at the power charger and configured to generate visible light emitted upward toward a rear surface of the mobile device, and a light guide plate extension section configured to connect the first sterilization light generator and the second sterilization light generator and configured to generate visible light laterally emitted to a lateral surface of the mobile device.

In some implementations, the mobile bidirectional sterilization device can include a second sterilization light generator provided at a center fascia charger configured to charge a mobile device by connecting vehicle power and configured to generate visible light emitted upward toward a rear surface of the mobile device, and a first sterilization light generator provided at a console bracket positioned above a center fascia charger to be separated therefrom and configured to generate visible light emitted downward toward a front surface of the mobile device.

In some examples, the visible light may have a 405 nm wavelength of generated from a light-emitting diode (LED) mounted on a printed circuit board (PCB) substrate.

In some examples, the downward, upward, and lateral emission may be generated in a light guiding plate made of a light guiding film configured to diffuse the visible light while forming a traveling path of the visible light.

In some implementations, the light guide plate may diffuse the visible light using a light emitting surface coated with optical ink and include a reflector configured to reflect the visible light to a surface opposite to the light emitting surface.

In some implementations, the light guiding plate may form the light guide plate extension section as a curved connection section.

In some implementations, the cover can be attached with a hinge.

The present disclosure is also directed to a vehicle equipped with a mobile bidirectional sterilization device, which includes a center fascia, a center fascia charger which charges a mobile device and in which visible light of a second light-emitting diode (LED) is diffused in a second light guiding plate made of alight guiding film and is emitted toward a rear surface of the mobile device, and a console bracket which is positioned above the center fascia charger and in which visible light of a first LED is diffused in a first light guiding plate made of a light guiding film and is emitted toward a front surface of the mobile device.

In some implementations, the center fascia charger may be built-in and provided at the center fascia and include a charging unit configured to charge the mobile device and a heat dissipation fan configured to cool heat generated by the charging unit.

In some examples, a removable mobile bidirectional sterilization device configured to charge the mobile device with vehicle power may be placed on the center fascia, the removable mobile bidirectional sterilization device may include a light guiding plate made of a light guiding film connected from the power charger to the cover through a curved connection section, and the visible light of the LED may be diffused from the light guiding plate and emitted to the front, rear and side surfaces of the mobile device which is placed in the power charger to be charged.

In some implementations, the cover can be attached with a hinge.

DETAILED DESCRIPTION

Figure 1:
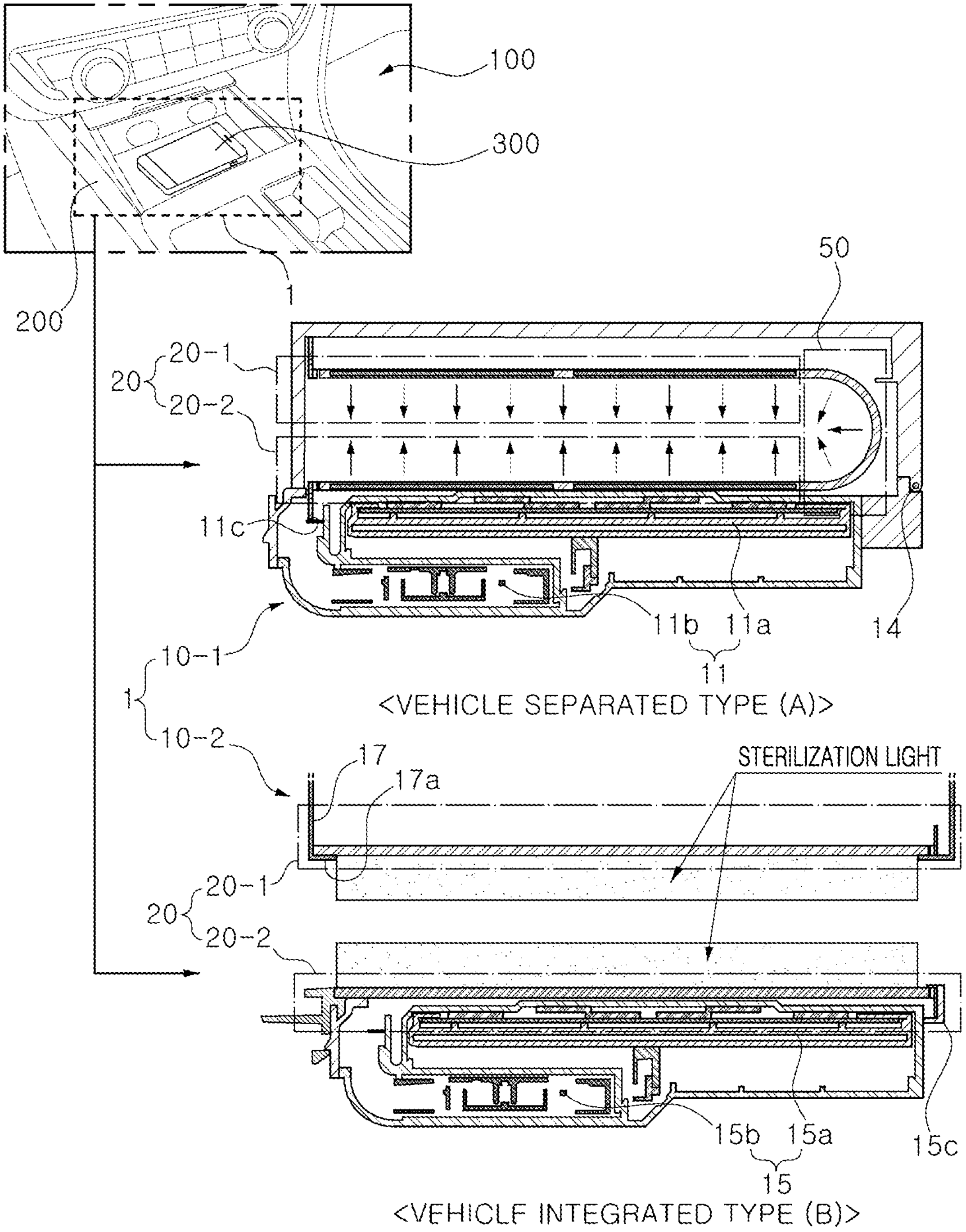
FIG. 1 is a diagram illustrating an example of a mobile bidirectional sterilization device applied to a vehicle.

Referring to FIG. 1, a mobile bidirectional sterilization device 1 performs a charging function of a mobile device 300 using vehicle power (i.e., a battery) in a center fascia 200 of a vehicle 100 and, simultaneously, implements enhancement of a health care function by removing germs transmitted by human hands through sterilization by visible light with a 405 nm wavelength. In this case, the center fascia 200 is a place where a gear shift lever is installed while being connected to a console box (i.e., an arm rest) on a side of a driver's seat of a vehicle.

To this end, the mobile bidirectional sterilization device 1 is divided into a removable mobile sterilization device 10-1 and a fixed mobile bidirectional sterilization device 10-2, the removable mobile bidirectional sterilization device 10-1 is a separated type from the vehicle 100 and may be carried and moved by a user, and the fixed mobile bidirectional sterilization device 10-2 is an integrated type with the vehicle 100 and is attached to the center fascia 200 of the vehicle 100 in a built-in type so as not to be carried and moved by the user. In this case, the center fascia 200 is merely one example, and the mobile bidirectional sterilization device 1 may be mounted using a crush pad or a console.

Specifically, the removable mobile bidirectional sterilization device 10-1 includes a power charger 11, a cover 13, a sterilization light generator 20, and a light guide plate extension section 50 and implements a charging function using the power charger 11 and a sterilization function using the sterilization light generator 20 and the light guide plate extension section 50.

In addition, in the removable mobile bidirectional sterilization device 10-1, an external lamp indicator indicating completion of charging and sterilization of the mobile device 300 may be equipped with the power charger 11 or the cover 13.

As one example, the power charger 11 is formed of a charging body in which a charging unit 11*a* and a heat dissipation fan 11*b* are embedded, the charging unit 11*a* is electrically connected to a jack or cable plugged into a power port installed in the vehicle 100 and charges the mobile device 300 and generates visible light from the sterilization light generator 20 with supplied power, and the heat dissipation fan 11*b* cools the power charger 11 against heat generated due to the supply of power at a lower portion of the charging unit 11*a*.

In particular, the charging unit 11*a* may supply power by plugging a jack or cable into the power port of the center fascia charger 15 installed in the center fascia 200.

In addition, in the power charger 11, a wireless charging pad capable of charging the mobile device 300 without plugging in a wire or plug may be applied to the charging unit 11*a*.

In some implementations, the cover 13 can be attached with a hinge. As one example, the hinged cover 13 is connected to one end portion of the charging body by a hinge pin 14 to form an integrated structure with the charging body of the power charger 11, and in a cover closed state, a cover inner space surrounding the mobile device 300 is formed as a quadrangular closed space like "□" together with an upper surface of the charging body of the power charger 11.

As one example, the sterilization light generator 20 includes a first sterilization light generator 20-1 and a second sterilization light generator 20-2, the first sterilization light generator 20-1 is placed on and fixed to a cover inner wall 13*a* protruding inward the hinged cover 13, and the second sterilization light generator 20-2 is coupled and fixed to a support protrusion 11*c* protruding from a side of the charging body of the power charger 11.

Figure 2:
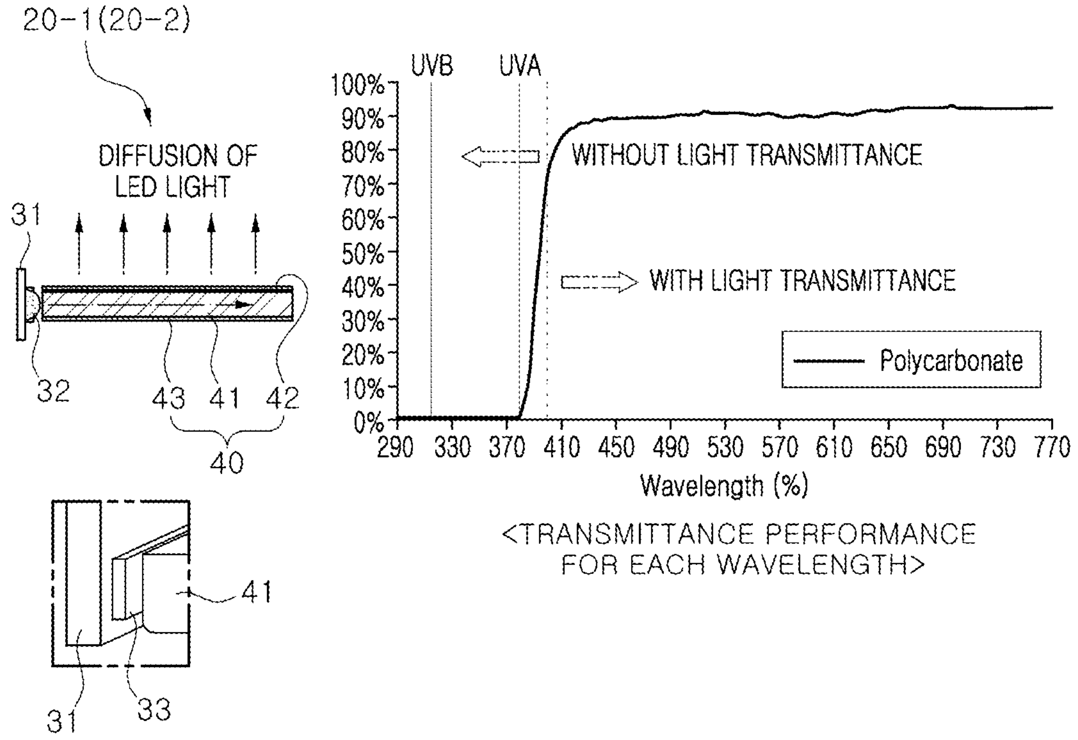
FIG. 2 is a detailed configuration diagram illustrating an example of a visible light-light-emitting diode (LED) unit and a diffusion unit constituting a sterilization light generator.
Figure 3:
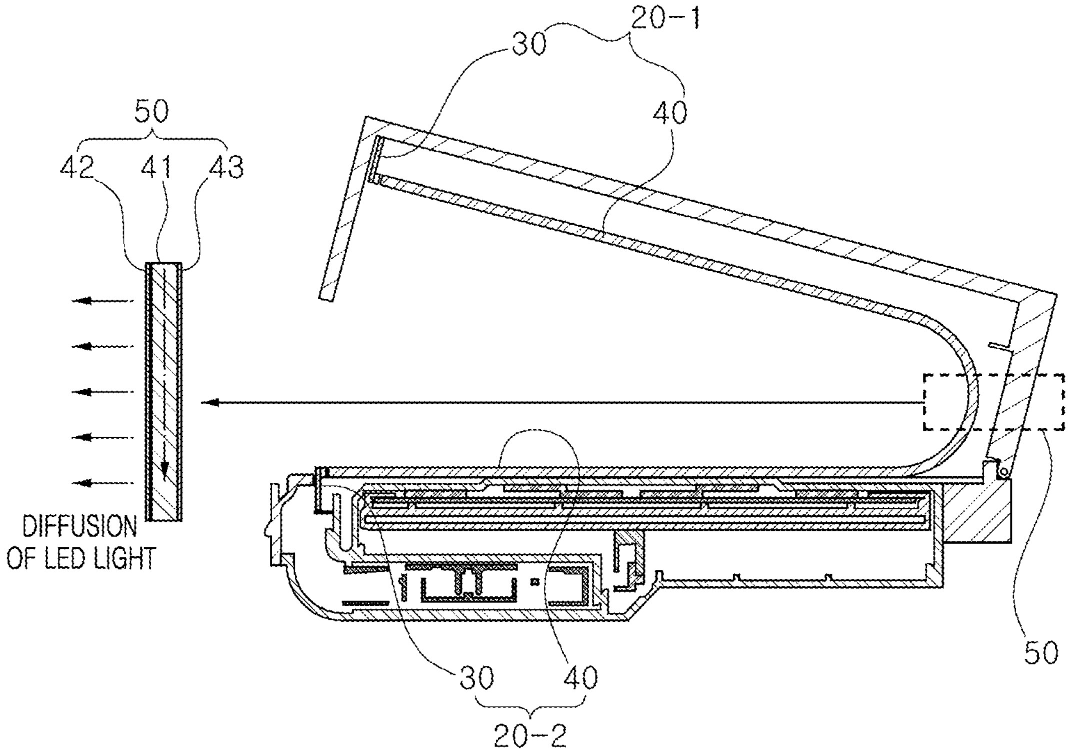
FIG. 3 is a detailed configuration diagram illustrating an example of a light guide plate extension section constituting the sterilization light generator.

As one example, by using one integral structure of the first and second sterilization light generators 20-1 and the second sterilization light generator 20-2, the light guide plate extension section 50 formed as a curved connection section in which a light guiding plate 41 of the first and second sterilization light generators 20-1 and 20-2 is connected (see FIGS. 2 and 3).

Thus, in the removable mobile bidirectional sterilization device 10-1, in a state in which the power charger 11 and the hinged cover 13 are closed, the first sterilization light generator 20-1 emits downward visible light from the hinged cover 13 toward the power charger 11, the second sterilization light generator 20-2 emits upward visible light from the power charger 11 toward the hinged cover 13, and furthermore, the light guide plate extension section 50 laterally emits visible light generated from the first and second sterilization light generators 20-1 and 20-2 from one side of the hinged cover 13 toward the cover inner space.

Specifically, the fixed mobile bidirectional sterilization device 10-2 includes the center fascia charger 15, a console bracket 17, and the sterilization light generator 20 and implements a charging function using the center fascia charger 15 and a sterilization function using the sterilization light generator 20.

In addition, in the fixed mobile bidirectional sterilization device 10-2, an external lamp indicator indicating completion of charging and sterilization of the mobile device 300 is applied to the center fascia charger 15 or the console bracket 17.

As one example, the center fascia charger 15 is formed of a charging body in which a charging unit 15*a* and a heat dissipation fan 15*b* are embedded, the charging unit 15*a* charges the mobile device 300 and generates visible light from the sterilization light generator 20 with power supplied through the center fascia 200 provided in the vehicle 100, and the heat dissipation fan 15*b* cools the center fascia charger 15 against heat generated due to the supply of power at the lower portion of the charging unit 15*a*.

In particular, the center fascia charger 15 may be provided with a power port into which a jack or cable is plugged to supply power to the charging unit 11*a*.

In addition, in the center fascia charger 15, a wireless charging pad capable of charging the mobile device 300 without plugging in a wire or plug may be equipped with the charging unit 15*a*.

As one example, the console bracket 17 is formed in a console portion on an upper side of the center fascia 200 so as to be separated from the center fascia charger 15 and forms a separation space with the center fascia charger 15 so that the mobile device 300 may be placed on an upper surface of the center fascia charger 15.

As one example, the sterilization light generator 20 includes the first sterilization light generator 20-1 and the second sterilization light generator 20-2, the first sterilization light generator 20-1 is placed on and fixed to a bracket protrusion 17*a* protruding inward the console bracket 17, and the second sterilization light generator 20-2 is coupled and fixed to the support protrusion 15*c* protruding from a side of the charging body of the center fascia charger 15.

Thus, in the fixed mobile bidirectional sterilization device 10-2, in a state in which the center fascia charger 15 and the console bracket 17 are separated, the first sterilization light generator 20-1 emits downward visible light from the console bracket 17 toward the center fascia charger 15, and the second sterilization light generator 20-2 emits upward visible light from the center fascia charger 15 toward the console bracket 17.

Referring to FIG. 2, each of the first and second sterilization light generators 20-1 and 20-2 includes the visible light-LED unit 30 and a light diffusion unit 40 as the same components.

Hereinafter, when the visible light-LED unit 30 is applied to the first sterilization light generator 20-1, a description is made as a first printed circuit board (PCB) substrate 31, a first LED 32, and a first light guiding plate bonding portion 33, and when the visible light-LED unit 30 is applied to the second sterilization light generator 20-2, a description is made as a second PCB substrate 31, a second LED 32, and a second light guiding plate bonding portion 33, but the description will be made as the PCB substrate 31, the LED 32, and the light guiding plate bonding portion 33 without distinction therebetween.

Specifically, the visible light-LED unit 30 includes the PCB substrate 31, the LED 32, and the light guiding plate bonding portion 33. In this case, the PCB substrate 31 is a typical component on which various electric device parts including semiconductors are integrated to generate visible light.

As one example, the PCB substrate 31 is electrically connected to supply power from the power charger 11 and the center fascia charger 15 and generates visible light by controlling a current flow with respect to the LED 32. The LED 32 is electrically connected to the PCB substrate 31 to generate visible light with a 405 nm wavelength. The light guiding plate bonding portion 33 connects the light guiding plate 41 of the light diffusion unit 40 and, to this end, attaches the light guiding plate 41 to an LED case in a state of facing a front surface of the LED 32 using the LED case.

In particular, referring to transmittance performance for each wavelength in FIG. 3, there is an example of solving a problem of directivity and transmittance of the existing light which are caused by UVC light with a wavelength ranging from 100 nm to 280 nm not having light transmittance because the 405 nm wavelength of the visible light has light transmittance.

Specifically, the light diffusion unit 40 includes the light guiding plate 41, optical ink 42, and a reflector 43.

As one example, since the light guiding plate 41 is made of a light guiding film and has a predetermined width and a predetermined length, the light guide plate 41 connects a traveling path of the visible light coming from one end thereof facing the LED 32 to the other half, and a light emitting surface is formed in which the visible light diffuses to the outside while passing through the traveling path. In this case, the light guiding film is manufactured through a roll stamping process using an extruded original sheet.

In addition, the optical ink 42 is applied or coated on the light emitting surface formed on one surface of the light guiding plate 41 to increase a light diffusion effect of the visible light, and the reflector 43 is overlaid or attached to the other surface of the light guiding plate 41 (that is, a surface to which the optical ink 42 is not coated) so that the visible light may be completely directed only toward the light emitting surface. In this case, an aluminum material may be applied to the reflector 43.

Referring to FIG. 3, the light guide plate extension section 50 is the curved connection section and forms one integrated structure in which the first and second sterilization light generators 20-1 and 20-2 are connected to each other in a "U" shape. Thus, the number of light diffusion units 40 may be reduced from two units applied to the first sterilization light generator 20-1 and the second sterilization light generator 20-2 to one unit.

However, when the light diffusion unit 40 is one, a length of the light diffusion unit 4 is longer as much as a length of the curved connection section compared to the case of two light diffusion units.

Therefore, the light guide plate extension section 50 includes the light guiding plate 41, the optical ink 42, and the reflector 43 as the same components of the light diffusion unit 40.

Figure 4:
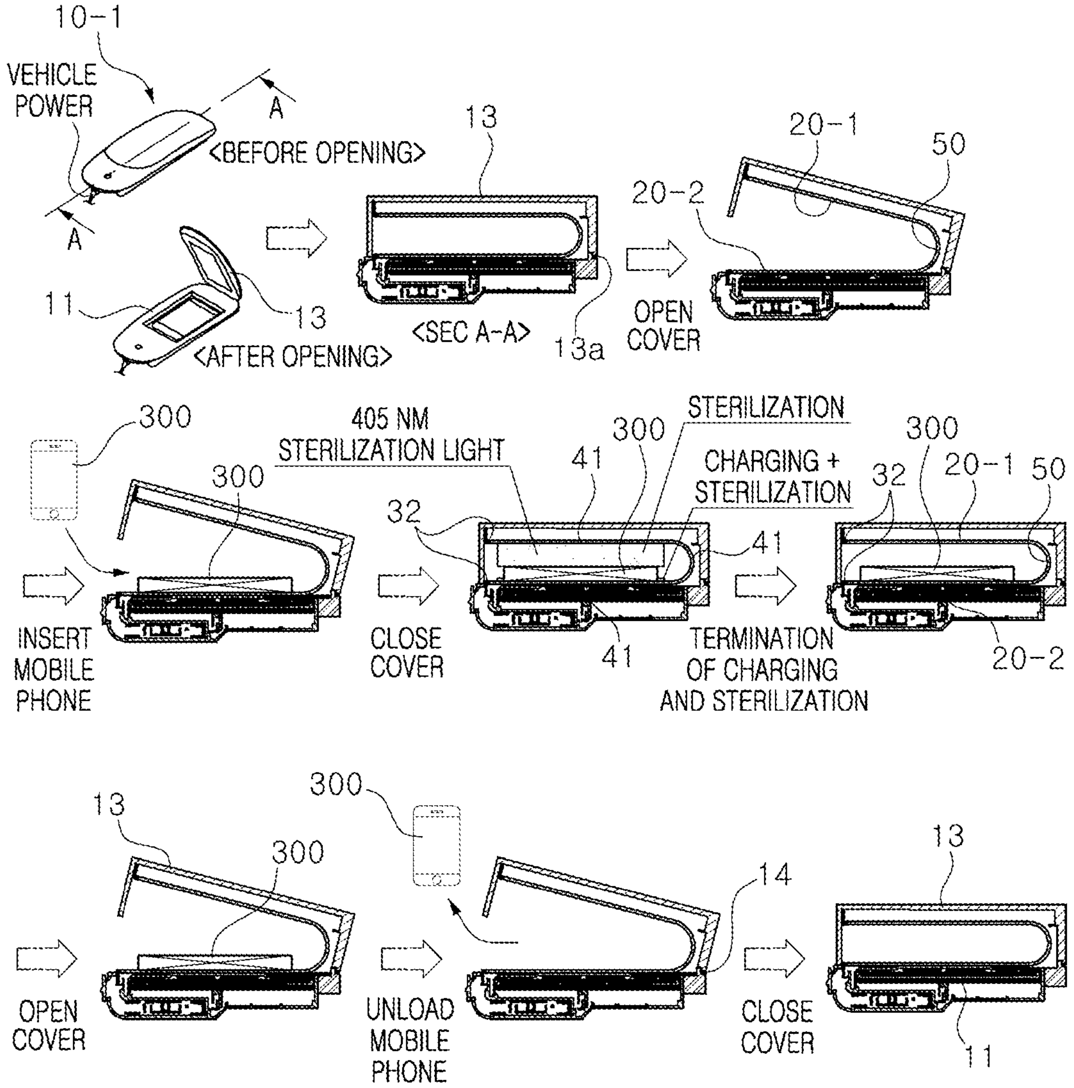
FIG. 4 is a diagram illustrating an example in which a vehicle removable-type mobile sterilization device of the mobile bidirectional sterilization device is used in a vehicle.
Figure 5:
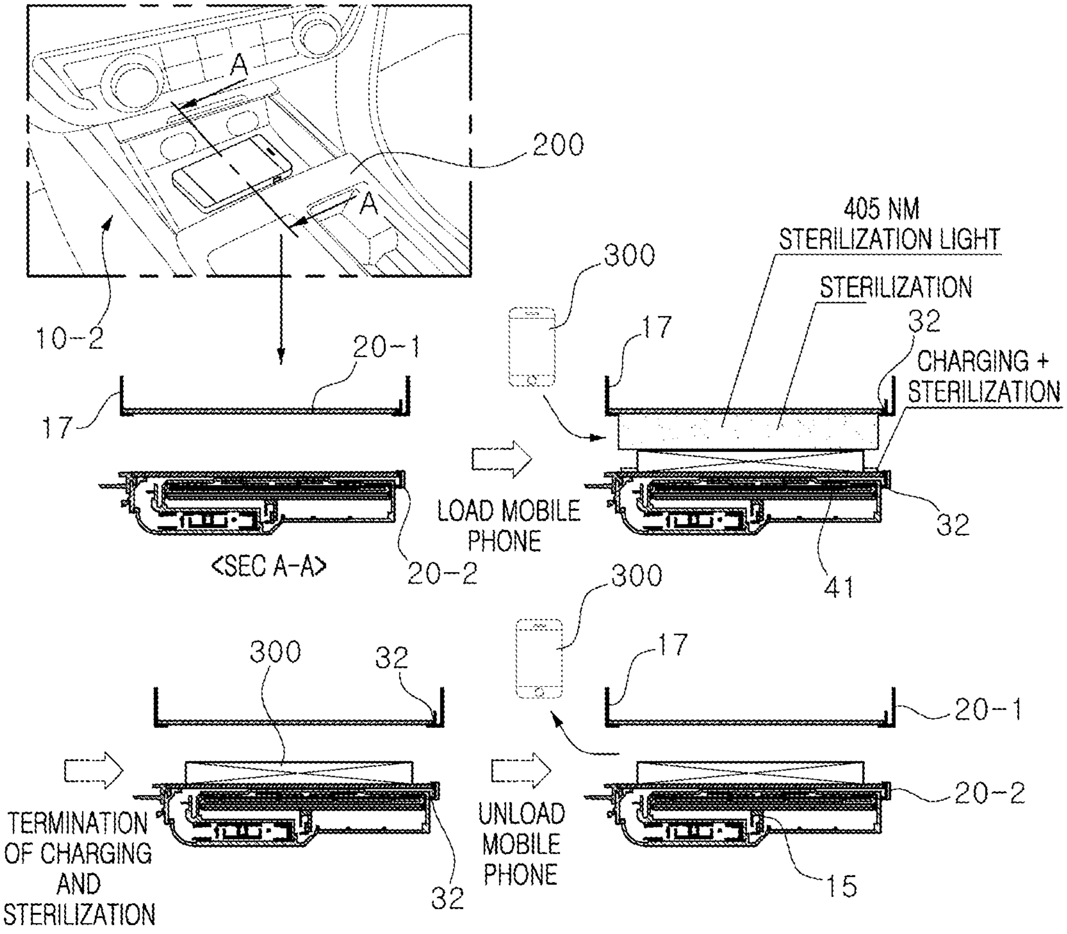
FIG. 5 is a diagram illustrating an example in which a vehicle integrated-type mobile sterilization device of the mobile bidirectional sterilization device is used in the vehicle.

Meanwhile, FIGS. 4 and 5 show a state of the use of the mobile bidirectional sterilization device 1.

Referring to the removable mobile bidirectional sterilization device 10-1 of FIG. 4, the removable mobile bidirectional sterilization device 10-1 is placed on the center fascia 200, a power cable or jack is inserted into a connector of the power charger 11 to supply vehicle power, and the hinged cover 13 is moved up by the medium of the hinge pin 14 to expose an upper surface of the power charger 11 to the outside.

Then, when the mobile device 300 is placed on the light guiding plate 41 of the second sterilization light generator 20-2 exposed on the upper surface of the power charger 11 and then the hinged cover 13 is moved down to form the cover inner space as an airtight space, battery charging of the mobile device 300 is performed by the charging unit 11*a* of the power charger 11. In this case, the heat dissipation fan 11*b* is driven to cool heat generated due to the charging process.

Simultaneously, the airtight space of the power charger 11 and the hinged cover 13 is filled with downward visible light which is emitted from the LED 32 of the first sterilization light generator 20-1 provided in the hinged cover 13 and is emitted downward into the cover inner space due to light diffusion by the light guiding plate 41 of the light diffusion unit 40, upward visible light which is emitted from the LED 32 of the second sterilization light generator 20-2 provided in the power charger 11 and is emitted upward the cover inner space of the due to light diffusion by the light guiding plate 41 of the light diffusion unit 40, and lateral visible light which is emitted toward an inside of the cover inner space due to light diffusion by the light guiding plate 41 of the light guide plate extension section 50 positioned on one side of the hinged cover 13.

Then, since all surfaces of the mobile device 300 are sterilized through the downward visible light, the upward visible light, and the lateral visible light in the cover inner space, upward, downward, and lateral light diffusion by the two light sources and the light guiding film significantly enhances sterilization effect so that it is possible to enhance a health care function by removing germs.

Then, when the completion of charging and sterilization of the mobile device 300 is confirmed by the external lamp indicator, the hinged cover 13 is moved up again to open the cover inner space, the mobile device 300 which is charged and sterilized is unloaded, and then the hinged cover 13 is moved down again.

Referring to the fixed mobile bidirectional sterilization device 10-2 of FIG. 5, when the mobile device 300 is placed on the center fascia charger 15 of the center fascia 200, battery charging is performed by the charging unit 15*a* of the center fascia charger 15. In this case, the heat dissipation fan 15*b* is driven to cool heat generated due to the charging process.

Simultaneously, due to light which is emitted from the LED 32 of the first sterilization light generator 20-1 provided in the console bracket 17 forming a separation space with the center fascia charger 15 and is diffused by the light guiding plate 41 of the light diffusion unit 40, the separation space is filled with downward visible light emitted downward the separation space and upward visible light emitted from the LED 32 of the second sterilization light generator 20-2 provided in the center fascia charger 15 and emitted upward the separated space due to light diffusion by the light guiding plate 41 of the light diffusion unit 40.

Then, since the mobile device 300 is entirely sterilized through the downward visible light and the upward visible light in the separation space, upward and downward light diffusion by the two light sources and the light guiding film enhances sterilization effect so that it is possible to enhance a health care function by removing germs.

Thereafter, when the completion of charging and sterilization of the mobile device 300 is confirmed through the external lamp indicator, the mobile device 300 is unloaded from the center fascia charger 15.

As described above, the mobile bidirectional sterilization device 1 used in the vehicle 100 can include the removable mobile bidirectional sterilization device 10-1 in which the light guiding plate 41 made of the light guiding film is connected from the power charger 11 to the hinged cover 13 through the curved light guide plate extension section 50 to emit the visible light from the LED 32 to the front, rear, and lateral surfaces of the mobile device 300 or the fixed mobile bidirectional sterilization device 10-2 in which the light guiding plate 41 made of the light guiding film emits the visible light of the LED 32 to the rear and front surfaces of the mobile device 300 at the console bracket 17 and the center fascia charger 15, solves the problem of harmfulness to the human body and the problem of directivity and transmittance due to an omnidirectional sterilization effect of the mobile device 300 by the visible light with a 405 nm wavelength and, particularly, maximizes an sterilization effect by an amount of light and reduces a production cost due to energy amplification of the visible light by the light guide plate extension section 50.

In accordance with a mobile bidirectional sterilization device applied to a vehicle according to the present disclosure, due to sterilization by visible light with a 405 nm wavelength, the problem of harmfulness to the human body and the problem of light directivity and transmittance can be solved.

In addition, in accordance with the mobile bidirectional sterilization device, by increasing a sterilization effect by light diffusion of the light guiding film in upward, downward, and lateral directions from two light sources emitting the visible light in two directions of a mobile device, it is possible to enhance a health care function and increase marketability by removing germs spread by human hands.

In addition, in accordance with the mobile bidirectional sterilization device, by employing a curved connection structure of the light guiding film, the two light sources are integrated and energy of the two light sources at upper and lower portions is amplified by a curved surface, it is possible to maximize a sterilization effect by the amount of light and to reduce a production cost.

What is claimed is:

1. A mobile bidirectional sterilization device, comprising:
- a power charger configured to supply power to a mobile device by utilizing vehicle power;
- a cover configured to open the power charger;
- a first sterilization light generator provided at the cover and configured to emit first visible light in a first direction toward a first surface of the mobile device;
- a second sterilization light generator provided at the power charger and configured to emit second visible light in a second direction toward a second surface of the mobile device; and
- a light guide plate extension connecting the first sterilization light generator to the second sterilization light generator and configured to emit third visible light in a third direction to a third surface of the mobile device,
- wherein each of the first sterilization light generator and the second sterilization light generator includes (i) a light-emitting diode (LED) configured to generate visible light and (ii) a light guiding plate configured to guide emission of the visible light, and
- wherein the light guiding plate is configured to diffuse the visible light using a light emitting surface coated with optical ink.

2. The mobile bidirectional sterilization device of claim 1, wherein a wavelength of each of the first, second, and third visible lights is 405 nm.

3. The mobile bidirectional sterilization device of claim 1, wherein:
- the LED is mounted on a printed circuit board (PCB) substrate, and
- the light guiding plate defines a traveling path of the visible light.

4. The mobile bidirectional sterilization device of claim 3, wherein the light guiding plate includes a light guiding film configured to diffuse the visible light.

5. The mobile bidirectional sterilization device of claim 1, wherein the light guiding plate provides a reflector configured to reflect the visible light on a surface opposite to the light emitting surface.

6. The mobile bidirectional sterilization device of claim 3, wherein the light guiding plates of the first and second sterilization light generators define the light guide plate extension as a curved surface connection section.

7. The mobile bidirectional sterilization device of claim 1, wherein the cover is a hinged cover that is attached via a hinge.

* * * * *